United States Patent [19]

Lilley

[11] Patent Number: 4,554,823

[45] Date of Patent: Nov. 26, 1985

[54] METHOD FOR BURNING RATE CHARACTERIZATION OF SOLID PROPELLANTS

[75] Inventor: Jay S. Lilley, Huntsville, Ala.

[73] Assignee: The United States of America as represented by the Secretary of the Army, Washington, D.C.

[21] Appl. No.: 624,063

[22] Filed: Jun. 25, 1984

[51] Int. Cl.⁴ .......................................... G01M 15/00
[52] U.S. Cl. ..................................................... 73/116
[58] Field of Search ...................... 73/116, 115, 117.3, 73/117.4; 431/13

[56] References Cited

U.S. PATENT DOCUMENTS 3,373,564  3/1968  Maybin ............................. 73/116 X
4,409,821 10/1983  Battles et al. ......................... 73/116

OTHER PUBLICATIONS

Brooks, W. T., "Proposed Standardized Method for Correlating Subscale Motor Burn Rates," CPIA Publication No. 300, Chemical Propulsion Information Agency, Laurel, MD, May 1979.
Brooks, W. T., "JANNAF Workshop on Burn Rate Determination Methodology," Chemical Propulsion Information Agency, Laurel, MD, Jul. 1981, pp. 255–267.
Brooks, W. T., Workshop Report; "Burn Rate Determination Methodology," CPIA Publication No. 347, Chemical Propulsion Information Agency, Laurel, MD, Oct. 1981, pp. 183–191.
Brooks, W. T., Workshop Report; "Burn Rate Determination Methodology," Chemical Propulsion Information Agency, Laurel, MD, Mar. 1982, pp. 247–253.

Primary Examiner—Jerry W. Myracle
Attorney, Agent, or Firm—Anthony T. Lane; Robert P. Gibson; Freddie M. Bush

[57] ABSTRACT

A method for determining the burning rate of a propellant. The method involves the single firing of a subscale, propellant motor that has been modified so that the propellant motor has a tapered cylindrical port that produces a non-neutral pressure-time trace when burned. The pressure-time trace is initially progressive (pressure increases with time), and then regressive (pressure decreases with time). Unlike conventional motors, this motor operates over a range of burning rates; therefore, the burning rate behavior of the propellant can be characterized with a single motor firing. The burning rate of the propellant is extracted from the motor pressure-time history by a computer analysis package. The analysis package employs an optimization program which uses an internal ballistics model of the motor. The ballistics model is used to generate a theoretical pressure-time trace which can be compared with the digitized output signal from the actual motor. The optimization routine of the computer determines the propellant burning rate behavior by selecting the burning rate law which, when employed in the internal ballistics model of the motor, produces the best match between the computer generated and the actual motor pressure-time traces. Thus by using the tapered port motor and by reducing the data, the burning rate of a propellant can be characterized with a single motor firing.

7 Claims, 5 Drawing Figures

METHOD FOR BURNING RATE CHARACTERIZATION OF SOLID PROPELLANTS

DEDICATORY CLAUSE

The invention described herein may be manufactured, used, and licensed by or for the Government for governmental purposes without the payment to me of any royalties thereon.

BACKGROUND OF THE INVENTION

A major consideration in any propellant development program is the characterization of the burning rate. Typically, burning propellant strands and subscale motor firings have been the means by which this information has been obtained. Of the two methods, experience has shown that subscale motors provide the better approximation of actual full scale motor conditions. To characterize the burning rate of the propellant as a function of pressure, a minimum of two subscale motor firings are required. But more typically, to insure statistical accuracy, from 3 to 9 or more firings are performed.

The typical subscale motor is designed to produce a neutral pressure-time history, and thus operate at a relatively constant pressure and burning rate. The average burning rate over the duration of a motor firing is typically determined by dividing the web distance burned by the burn time. The determination of burn time varies throughout the industry, but is typically based on the intersection of an aft tangent bisector with the pressure-time trace of a motor. This method of determining burning rate takes little advantage of internal ballistic information available from a subscale motor firing. Therefore, each subscale motor firing produces only a single pressure-burning rate point based on a determination of average conditions during a motor firing. The burning rate behavior of the propellant is thus characterized by firing a series of subscale motors over a range of operation pressures to provide several pressure-time burning rate points.

There are two obvious shortcomings involved in using the conventional subscale motor to determine burning rate. These are:
1. Several motor firings are required to characterize a propellant.
2. Burning rate determinations do not fully utilize the available internal ballistic information.

Ballistic test motors that are used throughout industry may be, generally, classified as those that have neutral pressure-time traces, as noted hereinabove, and those that do not. For the neutral burning motors, a survey on burning rate determination methodology has been performed industry-wide and is discussed in detail by W. T. Brooks in "Proposed Standardized Method for Correlating Subscale Motor Burn Rates," CPIA Publication No. 300, Chemical Propulsion Information Agency, Laurel, MD, May 1979.

While neutral burning test motors are the most commonly used test motors in industry, some motors that have non-neutral traces are employed. Of these motors, a stepped grain motor has been employed that produces a pressure-time trace as a series of steps. Initially, the motor operates at a first relatively constant pressure for a period of time and then abruptly changes to lower pressures, sequentially, as the burning surface area periodically changes. Since the stepped grain motor operates essentially as a series of neutral burning motors incorporated into a single propellant grain, the methods used for analyzing neutral traces can be applied for characterizing the burning rate.

An externally burning propellant slab may also be used as the grain of the non-neutral test motor. The slab produces a regressive pressure-time trace. In the slab burner process the pressure-time trace of the motor is used to determine instantaneous burning rate data. The geometry of the slab is initially known and an internal ballistic model of the motor is used to track the geometric regression of the slab. The ballistic model is used at each point in time to determine the geometry required to satisfy the continuity equation for the given instantaneous operating pressure. The burning rate at a given time step is determined by considering the amount of web distance burned over the past time step that is required to produce the appropriate geometry to satisfy continuity. Thus, the motor produces a series of instantaneous burning rate points that correspond to the pressure-time trace. These data points are then curve fitted to obtain a burning rate law.

After considering the existing methodology for obtaining burning rate data from ballistic test motors, it is evident that a need exists for an improved method. The neutral-burning test motors are attractive because they are simple to manufacture, and the data reduction process that is required is straightforward. However, these motors have two major shortcomings. The first is based on the neutrality of the motor—the motor operates at a relatively constant pressure, and thus can produce only a single, average, burning rate-pressure data point. Therefore, several motor firings are required to characterize a propellant.

The second shortcoming occurs in the way by which the average burning rate is determined. Several methods of determining burning rate may be used. A problem arises because the value of burning rate determined from a given trace will vary with the reduction method employed. In fact, if the aft-tangent method is employed (which is the most common method used) the value of burning rate can vary with the person reducing the data. Hence, a problem exists because these burning rates are based on definitions that are somewhat arbitrary; therefore, the data is subject to the definition chosen. A detailed consideration of the variability introduced by the reduction method chosen is presented by W. T. Brooks in "Workshop Report; "Burn Rate Determination Methodology," CPIA Publication No. 347, Chemical Propulsion Information Agency, Laurel, MD, October 1981, pp. 261–277.

Regardless of the method employed to obtain the propellant burning rate, a neutral trace motor still produces only a single data point. This problem can be overcome by employing a non-neutral trace motor. However, the stepped grain motor analysis process is essentially the same as that for a neutral motor. Therefore, the use of this motor incorporates the shortcomings experienced in using a neutral motor. In addition, the number of data points produced by the step is limited to the number of steps incorporated in the stepped design.

The slab burner approach eliminates several of the problems encountered in the stepped grain motor. The motor has a regressive pressure-time trace and thus operates over a range of pressures. Thus a burning rate-pressure data point can be produced at each time step on the pressure-time trace. In addition, the burning rate data is produced by an internal ballistic model and thus is not subject to any arbitrary definitions. The slab burner does have the problem that the burning-rate data is extremely sensitive to the pressure data, as the burning rate is computed directly from the pressure-time data. Any noise, or fluctuations in the data will be directly reflected in the burning rate data. In addition, these errors will be introduced into the geometry model and thus further compound the error.

SUMMARY OF THE INVENTION

A system for and method of determining propellant burning rate from one motor firing. The system and method utilizes a subscale motor that is modified. The motor has a tapered cylindrical port which, when burned, produces a non-neutral pressure-time trace. The resulting pressure-time trace is initially progressive, and then regressive. Unlike conventional motors, this motor operates over a range of burning rates; therefore, the burning rate behavior of the propellant can be characterized with a single motor firing.

The burning rate behavior of the propellant is extracted from the motor pressure-time history by a computer analysis package. This package employs an optimization program which uses an internal ballistics model of the test motor. The ballistics model is used to generate a theoretical pressure-time curve which is subsequently compared with a digitized output pressure curve from a motor firing. An optimization routine determines the propellant burning rate behavior by selecting the burning rate law which, when employed in the internal ballistic model, produces the best match between the theoretical and the actual pressure-time output signals. Thus by using a modified test motor and by reducing the data, the burning rate of a propellant can be characterized with only one motor firing.

PREFERRED EMBODIMENT OF THE INVENTION

A subscale ballistic tapered motor, or tapered propellant motor, can be used in solving prior art problems encountered, as noted in the Background of the Invention, with sensitiivty to fluctuations in the output pressure from the motor during the time of propellant or motor burn. This output pressure with respect to time, when recorded, is denoted as a pressure-time trace or curve. This task is accomplished by optimizing a ballistic model in view of the pressure-time trace of the particular motor, thereby providing a substantial match between the optimized model and the actual trace which results in characterization.

Instead of deriving motor burning rate data directly from the pressure-time trace as is done in the slab burner method, the burning rate relationship is produced indirectly. The burning rate law for the particular propellant is generated from comparisons between characteristics of an internal ballistic model of the motor and the actual pressure-time output trace. Because an internal ballistic model coupled with the optimization scheme is used to produce the burning relationship, the results are driven by the entire pressure-time output trace and thus is relatively insensitive to minor fluctuations in the data. In addition, because the burning rate data produced by the method is generated by an internal ballistics model. Thus the resulting burning rate data is directly compatible with internal ballistic performance prediction codes.

Therefore, the system and method provides a unique means of determining the burning rate of a propellant. The method can be employed to characterize the burning rate of a propellant over a range of pressures with a single motor firing.

Figure 1:
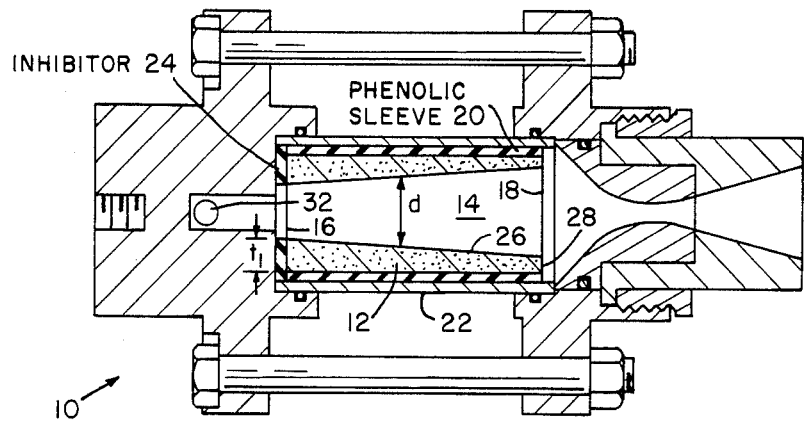
FIG. 1 is a simplified cross-sectional diagram of a typical subscale ballistic test motor having a tapered grain propellant.

Referring now to the drawings, FIG. 1 discloses a simplified view of a ballastic, tapered propellant motor cross-section. The motor results from a modification of a typical small ballistic test motor of a type which have been used in prior art for characterizing propellant grains that are neutral burning. The typical small ballistic test motor (not shown) has a constant diameter cylindrical port. A 2×4 motor which is typical of this motor has a grain length of 3.75 inches, the outside diameter of 2.00 inches and the web thickness of 0.25 inches. The grain burns on both ends as well as the interior and this configuration produces a nearly constant burning surface area vs web distance burned profile. The modified test motor (FIG. 1) uses the same basic configuration with the exception that the port has a linear taper, with the port diameter increasing from head to aft.

As shown in FIG. 1, motor assembly 10 has a tapered grain propellant 12 therein such that the port 14 thereof has a linear tapered surface, with the port diameter (d) increasing from head 16 to aft 18. This modified motor structure is cast in a phenolic sleeve 20. Phenolic sleeve 20 is designed so that the tapered motor can be cartridge loaded into the standard 2×4 motor case 22. This allows the motor to use the same firing hardware as a standard motor.

The outside diameter of the tapered grain 12 is 1.75 inches and the grain length is 3.75 inches. The web thickness t1 at the head end is 0.475 inches while at the aft end it is 0.225 inches. The head end of the grain can be inhibited by inhibitor 24 to provide a longer grain length at the end of the burn.

The burning surface versus web distance burned history of the tapered motor essentially can be considered to be composed of two distinctly different components. During the initial potion of the burn, the burning surface is composed of the interior surface 26 of the grain and the aft end 28. As the grain regresses, the burning surface area increases due to the cylindrical or conical surface 26 of grain 12 until the aft surface web burns out, producing the maximum burning surface area. For the remainder of the burn, the surface area decreases as the grain regresses.

This variable surface area versus web distance burned profile for the tapered motor is the feature which dramatically separates it from the conventional constant burning, motor. Thus, the modified motor operates over a range of pressures and exhibits a range of burning rates. Therefore, the major difference between the motors can be seen in the fact that a conventional motor firing produces one data point, an average burning rate at a given average pressure, while the tapered motor firing provides enough information to characterize the burning rate of a propellant over a range of pressures. A computer analysis package can be used to extract the burning rate-pressure from the output signal or trace.

The computer analysis package is composed of four independent Fortran programs. These are: a raw data conversion program, a data editing program, a burning rate analysis program, and a graphics output program. This analysis package was developed for operating on a Hewlett-Packard 1000, F series computer. This computer serves a dual role as a data acquisition and as a data reduction device, and it is used to control all phases of the burning rate analysis process.

Figure 3:
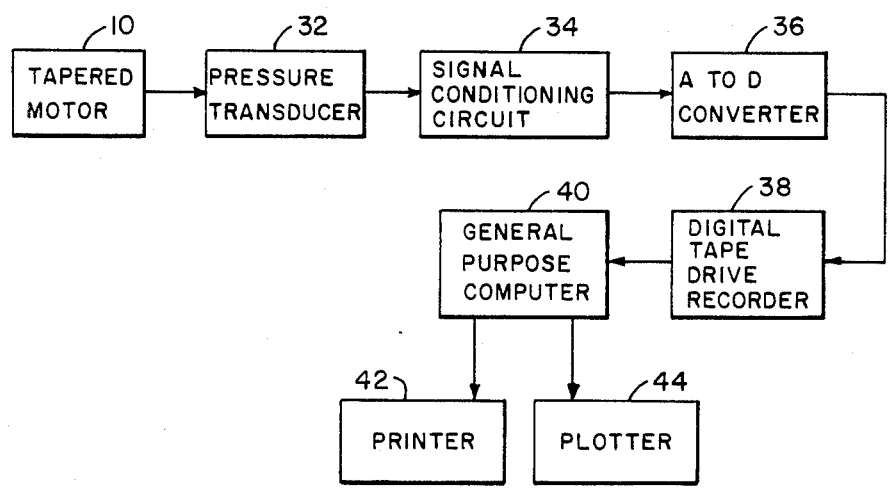
FIG. 3 is a simplified block diagram of the electrical circuit for providing burning rate characterization from a single test motor.

FIG. 3 discloses the electrical circuit operation. When a motor 10 is fired, the only instrumentation on the motor is a single pressure transducer 32. Transducer 32 is output coupled through signal conditioning circuit 34 to an analog to digital converter 36. Conditioning circuit 34 is merely an amplifier and filter circuit for filtering noise levels near the signal frequency ranges and amplifing the signal, as is routine in the art. The output of the A/D converter is then routed to a digital tape drive 38. When the motor is fired, the data from the pressure transducer is recorded in real time on the tape of drive recorder 38.

Figure 2:
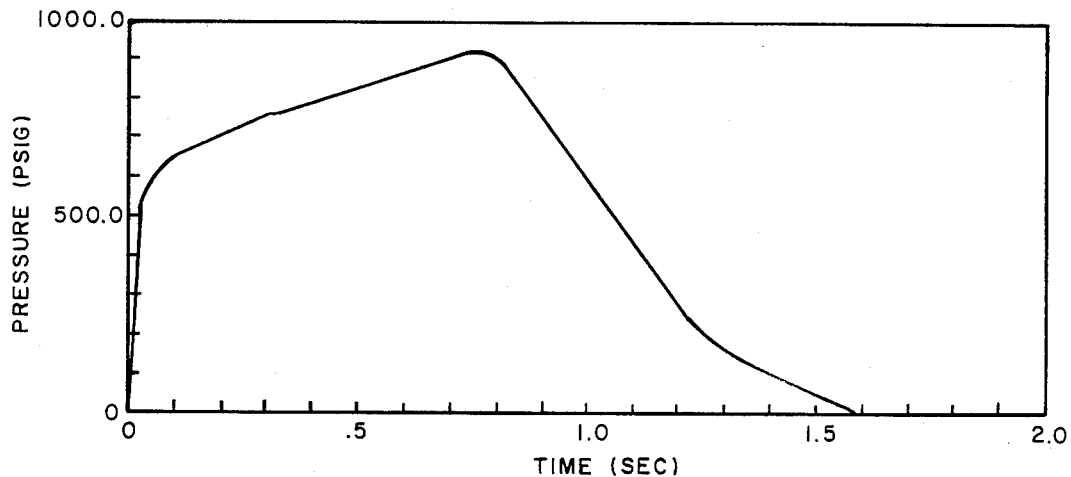
FIG. 2 is a graph of a typical tapered motor head pressure history where the head end is inhibited.

The digitized data on recorder 38 is coupled to computer 40 wherein it is retrieved by the raw data conversion program. The function of this raw data program is to convert the data from the tape from voltage into equivalent units of pressure (engineering units). After conversion, the pressure data along with the corresponding time steps are stored in a file. This data when traced is as shown generally in FIG. 2.

The raw pressure-time data is then retrieved by a data editing program. The function of this program is to direct the computer to strip out the pressure-time trace of the motor from the raw data. The pressure-time trace is located and the pressure points with the appropriate time steps are stored in the computer memory.

The pressure-time trace is then retrieved by a burning rate analysis program. The function of this program is to characterize the burning rate of the propellant tested. This characterization is accomplished by employing an optimization scheme. This analysis procedure is based on the assumption that the burning rate of the propellant essentially behaves according to one of the two user selected, two-parameter, burning rate laws. The selected burning rate law is incorporated in an internal ballistics model of the tapered motor. This model is used to generate a theoretical pressure-time history for the motor. This theoretical pressure-time trace is compared against the actual trace by determining the absolute area error. The optimization scheme is used to select the burning rate law parameters that minimize this error. The resulting output optimum burning rate law is considered to be representative of the propellant over the operating pressure range of the motor firing.

The burning rate analysis program produces the main set of tabular output for the computer analysis package. Included are details of the optimization routine, the optimum solution set, and the actual optimum theoretical pressure-time traces. The two pressure-time traces are stored in a file along with the optimum burning rate-pressure curve.

The two traces and the rate-pressure curve are then retrieved by the graphics output program. The function of this program is to provide graphics output from the burning rate analysis. More specifically, the graphics program produces a plot of the pressure-time traces and a rate-pressure plot of the optimum burning rate law.

The computer analysis package provides a self-contained data acquisition and reduction method. This system has no computational interfaces with an operator and thus is not subject to individual judgments. Thus this system is accurate, reliable, consistent, and provides a higher degree of data reproducibility than conventional methods.

Figure 4:
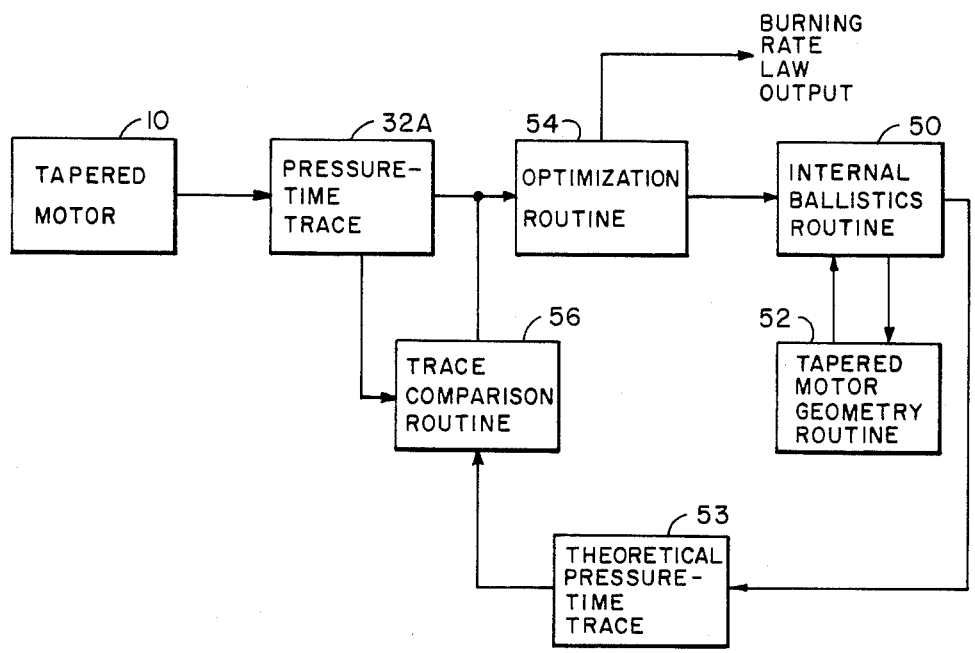
FIG. 4 is a block diagram or flow diagram depicting the process for obtaining the propellant burning rate characterization.

The key component of the computer analysis package is the burning rate analysis program. This program provides the means by which the pressure-time data from a tapered motor firing is used to characterize the burning rate of a propellant. A block diagram of the burning rate analysis program is shown in FIG. 4.

The burning rate analysis program has two user selecting burning rate laws. The first burning rate law is the traditional power law which has the form:

$$r_b = CP^N \qquad (1)$$

Table I is an alphabetical list of the definitions and symbols used in equation (1) and all of the equations. The rate law of equation (1) is the one most widely used throughout the industry and is an accurate representation of the burning rate behavior of a wide variety of propellants. This expression is typically considered to apply over a specified pressure range for a given propellant.

The second available burning rate law has the form:

$$1/r_b = A/P + B/P^{\frac{1}{3}} \qquad (2)$$

This burning rate law was initially developed by Summerfield for a Granular Diffusion Flame (GDF) combustion model. The utility of this burning rate law is evident in the fact that on a log-log grid the rate-pressure plot has a curved profile as opposed to the linear plot of the traditional power law. This feature is useful in modeling the burning rates of propellants that experience a change in the burning rate exponent as a function of pressure, commonly known as an exponent break.

Consider the following definition of burning rate exponent N:

$$N = \frac{\partial \ln r_b}{\partial \ln P} \qquad (3)$$

It can be shown that for burning rate law (2):

$$N = \frac{A + \frac{1}{3} BP^{\frac{1}{3}}}{A + BP^{\frac{1}{3}}} \qquad (4)$$

It is evident that as P approaches zero, N approaches 1, and as P approaches infinity, N approaches $\frac{1}{3}$. Thus, this rate law can be used to model propellants with an exponent range of 1 to $\frac{1}{3}$ whose exponent decreases with pressure. Therefore, this burning rate law can be used to model some of the propellants which experience an exponent break. This rate law models variable exponent behavior with only two parameters A and B.

The internal ballistics model or routine 50 (FIG. 4) of the tapered motor is used by the burning rate analysis program of the computer to generate a theoretical pressure-time trace from a given set of burning rate parameters. The function of this routine is to provide an indirect method by which a prospective burning rate law can be evaluated by comparison against experimental results. Since this routine is used with every set of burning rate parameters considered, a simple model minimizes program execution time.

A one-dimensional, unsteady model provides a simple internal ballistics model for the system with the following assumed limitation or condition:
1. The flow in the motor is one-dimensional, adiabatic, and unsteady.
2. The combustion products behave as a calorically and thermally perfect gas.
3. The combustion temperature of the propellant and the molecular weight and specific heat ratio of the combustion products are constant throughout the grain and for all time.
4. The mass addition process occurs instantaneously with no radial component of velocity.
5. The propellant regresses normal to itself, and at each give time-step the entire grain regresses at an average burning rate.
6. The nozzle throat area is constant over the entire burn time.
7. The flow through the nozzle is isentropic.

To generate a theoretical pressure-time trace, the internal ballistic model requires a set of geometric and thermodynamic inputs and the two burning rate parameters A and B. The model produces the theoretical pressure-time trace by deermining the head-end pressure of the motor at discrete points in time. This solution is found by satisfying continuity at each time-step. The grain of the motor is considered to be composed of a series of mass addition elements. The mass flow rate leaving a given element (the ith element) is given by:

$$M_i = M_{i-1} + M_{gen_i} - M_{stored_i} \quad (5)$$

where, $$M_{gen_i} = \rho_p A_{b_i} r_{b_i} \quad (6)$$

The burning rate of equation (6) is determined from the selected burning rate law. Also note the unsteady nature of the solution is reflected in the mass storage rate term. Thus, the mass flow rate of the entire grain is given by:

$$M_{grain} = \sum_{i=1}^{e} M_i \quad (7)$$

However, the mass flow rate of the motor is also equal to the mass flow rate of the nozzle which is given by:

$$M_{nozzle} = \frac{g_c A_t P_{\phi n}}{C^*} \quad (8)$$

In order for continuity to be satisfied, the mass flow rate of the grain must equal that of the nozzle. Now both mass flow rates are entirely determined at each time-step by the selection of head-end pressure. Thus, the head-end pressure at each time-step is determined by finding the pressure for which the two mass flow rates are equal.

After determining the head-end pressure at a given time-step, the grain is regressed. Equation (9) is used to determine the new value of web distance burned:

$$\tau(t + \Delta t) = \tau(t) + r_b(t)\Delta t \quad (9)$$

where $$\bar{r}_b(t) = 1/e \sum_{i=1}^{e} \bar{r}_{b_i}(t) \quad (10)$$

After the new burn distance has been obtained, the tapered motor geometry routine 52 (FIG. 4) is employed. This routine determines the flow areas, the volume, and burning surface area of each mass addition element as a function of web distance burned.

The solution procedure for the head-end pressure is repeated at each time step until the nozzle unchokes. The result is a theoretical head-end pressure-time trace 53 (FIG. 4).

The driving component of the burning rate analysis program is the optimization procedure 54 that is employed (FIG. 4). This is the means by which the characteristic burning rate law for the given propellant is selected.

The optimization procedure used is a pattern-search. This search is performed on the following four variables: A, B, $A_t/C^*$, and $P_{max}$. The pattern search is used to minimize the index of performance, IP, which is given by:

$$IP = \sum_{i=1}^{N_{tot}} |P_{xi} - P_{thi}|. \quad (11)$$

If $$N_{ex} \geq N_{th} \quad (12)$$

then $$N_{tot} \doteq N_{ex}; \quad (13)$$

and if $$N_{th} > N_{ex} \quad (14)$$

then $$N_{tot} = N_{th} \quad (15)$$

The value of IP, however, is essentially proportional to the absolute area error between the two traces (by $\Delta t$). Thus, the optimization route in effect minimizes the absolute trace area error. The value of IP is provided by the trace comparison routine 56.

The pattern-search optimization method belongs to a class of optimization procedures known as "hill-climbers". The hill-climber method locates a minimum on the solution surface by progressing along the local gradient vector. A major problem with this type of optimization method is the tendency to locate local extrema as opposed to the desired global optimum. Therefore, hill-climber routines are usually sensitive to the starting location of the search. It is important, therefore, to select a starting point for the search that is in the neighborhood of the global minimum.

The nature of the optimum solution is not totally unknown. Information is available from the experimental pressure-time trace and from the geometry of the test motor. An initial estimate on the ratio of throat area to characteristic velocity is given by:

$$A_t/C^* = \frac{1/g_c \, M_{pld} - \frac{(P_{xb}V_b - P_{xo}V_o)}{R_g T_c K}}{\int_{t_o}^{t_b} P_x dt} \quad (16)$$

where $$R_g = \frac{C^{*2}\gamma \frac{2}{(\gamma+1)} \frac{\gamma+1}{\gamma-1}}{T_c} \quad (17)$$

Note the solution is iterative in nature as $R_g$ and $A_t/C^*$ are dependent on each other.

The nature of the progressive-regressive pressure-time trace provides additional information due to the fact that the maximum operating pressure must correspond to a maximum burning surface area. Therefore, the burning rate at the maximum pressure can be determined by the following expression:

$$r_{bmax} = \frac{g_c A_t P_{max}}{C^* A_{bmax} \rho_p - \frac{P_{max} g_c}{R_g T_c K}} \quad (18)$$

With one burning rate-pressure point known, an important constraint is placed on the burning rate law. The two parameters A and B are no longer independent and the following relationships can be applied:

For the traditional power rate law:

$$A = e^{(\alpha_1 - B\alpha_2)} \quad (19)$$

where:

$$\alpha_1 = \ln r_{bmax} \quad (20)$$

and $$\alpha_2 = \ln P_{max} \quad (21)$$

For the GDF rate law:

$$A = \beta_1 - B\beta_2 \quad (22)$$

where $$\beta_1 = \frac{P_{max}}{r_{bmax}} \quad (23)$$

and $$\beta_2 = P_{max}^{\frac{3}{2}} \quad (24)$$

To initiate the pattern-search, the value of $A_t/C^*$ is set equal to the value produced by equation (16), the value of $P_{max}$ is set equal to $P_{xmax}$ and A and B are constrained by either equation (19) or equation (22) depending on the selected rate law. The values of $A_t/C^*$ and $P_{max}$ are held constant and a pattern-search is performed only on B. This search is a rotation of the burning rate curve about the maximum pressure burning rate point. A second pattern-search is then performed on B and $A_t/C^*$. Once again, the relationship between A and B is applied, and the value of $P_{max}$ is held constant. A third pattern search is then initiated on A, B, and $A_t/C^*$. In this case, A and B are considered as independent variables. Once again, $P_{max}$ is held constant.

The execution of the three pattern searches produces an interim optimum solution set, which is stored along with the corresponding index of performance. At this point, the pattern-search on $P_{max}$ is initiated. This search routine selects a new value of $P_{max}$ and that value is used to reinitialize the pattern-searches on the other three variables. The pattern-search on $P_{max}$ causes a translation of the maximum pressure burning rate point. Thus, the total pattern-search procedure of the computer produces a translation and rotation of the burning rate curve. The search routine on $P_{max}$ selects the value of $P_{max}$ which produces the interim solution set with the lowest index of performance. This set is the optimum solution for the entire pattern-search procedure. The burning rate law output represented by this optimum set is representative of the propellant tested. The optimum index of performance is a measure of how well the theoretical model compares with the actual results and thus, serves as an indication of the applicability of the burning rate law.

The overall procedure is dependent on a knowledge of the geometry of the motor at each time step. In particular, the accuracy of the method is dependent to some degree on the accuracy of program inputs. Specifically, the two major concerns are the accuracy of the values input for the throat area and for the dimensions of the grain.

Due to the nature of the motor, housing hardware, and the frequency of its use, the accurate determination of the throat area is important. For this reason $A_t/C^*$ was included as a variable in the pattern-search procedure. Some insight to the influence of $A_t$ on the analysis process is gained by considering the internal ballistics of the motor. At each time-step, the continuity equation for the motor can be approximated by:

$$\frac{g_c A_t P_{\phi n}}{C^*} = \rho_p A_b \bar{r}_b - \frac{d}{dt}(\bar{\rho}_c V) \quad (25)$$

The value of head-end pressure at each time-step is determined by satisfying this equation. Thus the accuracy of $A_t/C^*$ has a major influence on the internal ballistic solution.

Since the value of $A_t$ which is input is of questionable accuracy, the value of $A_t/C^*$ is considered a free variable in the pattern-search process. Thus the optimum solution set for a given motor firing includes an optimum $A_t/C^*$. This optimum ratio should reflect the actual conditions of the motor. Therefore, the results of the process should be insensitive to inaccuracy in the input value of $A_t$. A testing of the system with theoretical data provides results which indicate that the analysis method is insensitive to inaccuracy in the input value for $A_t$.

The second item of concern is the error introduced to the burning rate analysis process by uncertainties in the dimensions of the grain. A test of the system indicates that the error in the burning rate introduced by geometric uncertainty is within acceptable limits and can be ignored.

TABLE I

| SYMBOL | NOMENCLATURE |
|---|---|
| A | = Burning rate parameter (psia-sec/in psia$^{-N}$-in/sec) |

TABLE I-continued

| SYMBOL | NOMENCLATURE |
|---|---|
| $A_b$ | = Burning surface area (in$^2$) |
| $A_t$ | = Throat area (in$^2$) |
| B | = Burning rate parameter (psia$^{\frac{1}{2}}$ sec/in or dimensionless) |
| C | = Burning rate parameter for traditional power law (psia$^{-N}$-in/sec) |
| C* | = Characteristic velocity (ft/sec) |
| e | = Number of mass addition elements |
| $g_c$ | = Unit conversion factor 32.174 (lb$_m$/slug) |
| IP | = Index of performance (psia) |
| K | = Unit conversion factor 12 (in/ft) |
| M | = Mass flow rate of combustion products (lb$_m$/sec) |
| $M_{gen}$ | = mass flow rate of combustion products generated by the burning propellant surface (lb$_m$/sec) |
| $M_{stored}$ | = mass storage rate of combustion products (lb$_m$-sec) |
| $M_{pld}$ | = Mass of propellant loaded in the grain (lb$_m$) |
| N | = Burning rate exponent |
| $N_{ex}$ | = Number of pressure points in the actual pressure-time trace |
| $N_{th}$ | = Number of pressure points in the theoretical pressure-time trace |
| $N_{tot}$ | = Number of pressure points used to determine the index of performance |
| P | = Static pressure (psia) |
| $P_{max}$ | = Maximum theoretical operating pressure of the test motor (psia) |
| $P_{0n}$ | = Stagnation pressure of the nozzle (psia) |
| $r_b$ | = Burning rate (in/sec) |
| $\bar{r}_b$ | = Average burning rate over the grain (in/sec) |
| $\bar{r}_{bi}$ | = Average burning rate over the mass addition element (in/sec) |
| $R_g$ | = Ideal gas constant (ft$^2$/(sec$^2$-°R) |
| t | = time (sec) |
| $T_C$ | = Combustion temperature (°R) |
| V | = Free volume (in$^3$) |
| $\alpha_1$ | = Burning rate constraint constant (ln (in/sec)) |
| $\alpha_2$ | = Burning rate constraint constant (ln (psia)) |
| $\beta_1$ | = Burning rate constraint constant (psia-sec/in) |
| $\beta_2$ | = Burning rate constraint constant ((psia/$^{\frac{1}{2}}$) |
| $\gamma$ | = Specific heat ratio |
| $\Delta$ | = A difference in a quantity |
| $\bar{\rho}_g$ | = Average combustion product density through out the flow volume of the motor (lb$_m$/in$^3$) |
| $\rho_p$ | = Density of unburned solid propellant (lb$_m$/in$^3$) |
| ($\tau$ | = Web distance burned (in) |

SUBSCRIPTS
b = corresponds to the time of the burnout of the test motor grain
i = corresponds to conditions in the ith mass addition element
grain = corresponds to conditions in the propellant grain
max = maximum value
nozzle = corresponds to conditions in the nozzle
o = corresponds to the time of grain ignition
th = theoretical value
x = actual measured value A series of experimental tests have been conducted. In each series, a number of conventional motors, containing propellant from the same formulation, were fired to obtain burning rate data over a range of pressures. In addition, tapered motors cast from the same propellant were also fired. These tapered motors were operated over the same pressure range as that covered by the conventional firings. Both composite and double base propellants were tested.

Figure 5:
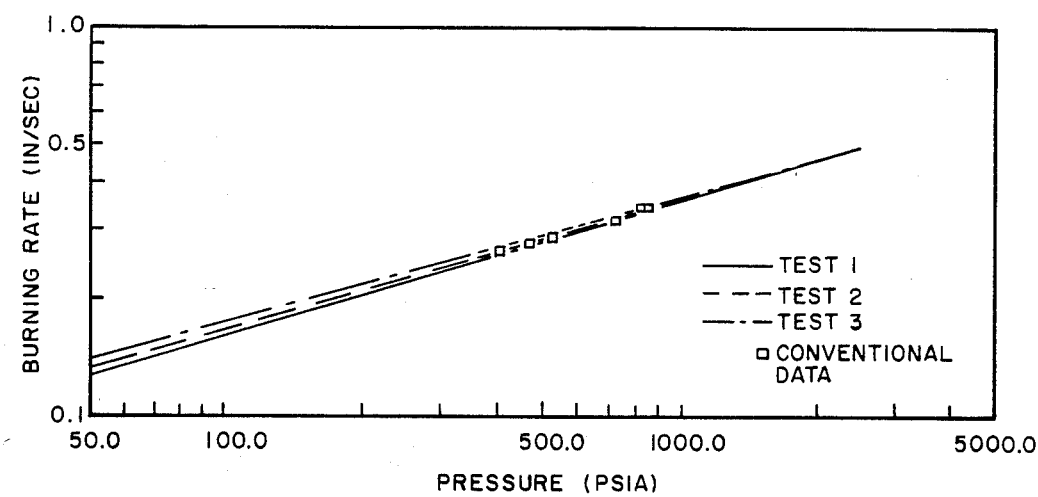
FIG. 5 is a typical graph of motor burning rate versus pressure data for several tapered propellant motors with conventional motor points shown.

Three typical burning rate curves resulting from the processing of tapered motor firings from a typical test series are plotted on the same set of axes as conventional motor data for the same propellant and is shown in FIG. 5. In all of the cases, the absolute area error was less than 4.3%. These results indicate that the optimization, when incorporated in the internal ballistics model of the test motor, produces an accurate representation of the ballistic performance of the motor.

Thus, a method for the characterization of the burning rate of solid propellants is disclosed that has a valid optimization procedure. The method is relatively insensitive to errors in the input value of throat area. The level of error introduced by uncertainties in critical grain dimensions was within acceptable limits. The method has been employed on both composite and double base propellants with successful results. The burning rate law produced by the method, which employs only one motor firing, is comparable with conventionally reduced data produced by a series of firings. Thus, the burning rate of a propellant can be characterized over a pressure range with a single motor firing.

Although a particular embodiment and form of this invention has been illustrated, it is apparent that various modifications and embodiments of the invention may be made by those skilled in the art without departing from the scope and spirit of the foregoing disclosure. Accordingly the scope of the invention should be limited only by the claims appended hereto.

I claim:

1. A system for providing characterization of burning rate of solid propellant motors from a single motor firing, comprising: a tapered solid propellant motor for providing a variable burning rate output, an analog to digital converter having an input and an output, a single pressure transducer coupled between said motor and said converter input for sensing variable head gas pressure output from said motor and coupling an output signal indicative thereof to said converter, means coupled to said converter output and responsive to the output therefrom for providing an output signal that defines the burning rate of said motor in response to output pressure.

2. A system for providing characterization of burning rate of solid propellant motors from a single motor firing, as set forth in claim 1 wherein said tapered propellant motor has cylindrical outer surface, and has a tapered, conical inner surface which defines a port diameter that increases from a first, head, end to a second, aft, exhaust end thereof.

3. A system for providing characterization of burning rate of solid propellant motors from a single motor firing as set forth in claim 2 wherein said first end is inhibited from burning at the outermost end thereof.

4. A system for providing characterization of burning rate of solid propellant motors from a single motor firing as set forth in claim 2 wherein said tapered solid propellant motor has an interior, burning area that increases during initial burning until the aft surface web burns out and then decreases as the propellant grain decreases.

5. A method of characterizing the burning rate of a solid propellant motor, comprising the steps of:
 shaping a grain propellant to have a cylindrical outer surface and a tapered, conical inner surface;
 placing the shaped propellant into a motor housing having a cylindrical inner support structure so that the base portion of the conical inner surface is at the aft or exhaust end of the motor housing;
 igniting the inner conical surface of the propellant motor,
 recording in real time the head end gas pressure from the propellant motor, and
 generating a characteristic curve comparable to the output pressure-time recording from the motor.

6. A method as set forth in claim 5 and further comprising the step of:
 inhibiting the burning rate of the propellant at the larger end of the propellant.

7. A method of characterizing the burning rate of a solid propellant motor, comprising the steps of:
shaping a grain propellant to have a cylindrical outer surface and a tapered, conical inner surface;
placing the shaped propellant into a motor housing having a cylindrical inner support structure so that the base portion of the conical inner surface is at the aft or exhaust end of the motor housing;
igniting the propellant motor;
generating a propellant pressure-time output signal that is initially progressive, then regressive;
converting the signal to a digital signal;
sequentially generating characteristic curves that are characteristic of the pressure-time signal; and
sequentially comparing the sequentially generated characteristic curves with the propellant pressure-time curves for obtaining an optimum match between the curves representative of burning rate characterization.

* * * * *

UNITED STATES PATENT AND TRADEMARK OFFICE
CERTIFICATE OF CORRECTION

PATENT NO. : 4,554,823
DATED : November 26, 1985
INVENTOR(S) : Jay S. Lilley

It is certified that error appears in the above—identified patent and that said Letters Patent is hereby corrected as shown below:

Column 7, line 41, the equation reading $$M_i = M_{i-1} + M_{gen_i} - M_{stored_i}$$

should read $$\dot{M}_i = \dot{M}_{i-1} + \dot{M}_{gen_i} - \dot{M}_{stored_i}$$

Column 7, line 44, the equation reading $$M_{gen_i} = \rho_p A_{b_i} r_{b_i}$$

should read $$\dot{M}_{gen_i} = \rho_p A_{b_i} \bar{r}_{b_i}$$

Column 8, line 5, that portion of the equation reading $r_b$ should read $\bar{r}_b$ Column 9, line 8, that portion of the equation reading $$\int_{t_o}^{t_b} P_x \, dt$$

should read $$\int_{t_o}^{t_b} P_x \, dt$$

UNITED STATES PATENT AND TRADEMARK OFFICE
CERTIFICATE OF CORRECTION

PATENT NO. : 4,554,823

DATED : November 26, 1985

INVENTOR(S) : Jay S. Lilley

It is certified that error appears in the above—identified patent and that said Letters Patent is hereby corrected as shown below:

Column 9, line 14, that portion of the right-hand part of the equation reading $$\frac{2}{(\gamma+1)}\frac{\gamma+1}{\gamma-1}$$ should read $$\frac{2}{(\gamma+1)}^{\frac{\gamma+1}{\gamma-1}}$$

Column 9, line 40, the right-hand part of the equation reading $$\ln r_{b_{max}}$$ should read $$\ln\ r_{b_{max}}$$

Column 9, line 43, the right-hand part of the equation reading $$\ln P_{max}$$ should read $$\ln\ P_{max}$$

UNITED STATES PATENT AND TRADEMARK OFFICE
CERTIFICATE OF CORRECTION

PATENT NO. : 4,554,823           Page 3 of 3
DATED     : November 26, 1985
INVENTOR(S): Jay S. Lilley It is certified that error appears in the above-identified patent and that said Letters Patent is hereby corrected as shown below:

Column 10, line 41, the right-hand part of the equation reading $(\bar{P}_c V)$ should read $(\bar{P}_g V)$

[SEAL]

Signed and Sealed this

Fifteenth Day of July 1986

Attest:

DONALD J. QUIGG

Attesting Officer

Commissioner of Patents and Trademarks